(12) United States Patent
Christensen et al.

(10) Patent No.: US 8,248,611 B2
(45) Date of Patent: Aug. 21, 2012

(54) HANDHELD OPTICAL MEASURING DEVICE AND METHOD OF USE

(75) Inventors: William M. Christensen, Hibbing, MN (US); Eugene Tokhtuev, Duluth, MN (US); Christopher J. Owen, Duluth, MN (US)

(73) Assignee: Ecolab USA Inc., St. Paul, MN (US)

( * ) Notice: Subject to any disclaimer, the term of this patent is extended or adjusted under 35 U.S.C. 154(b) by 308 days.

(21) Appl. No.: 12/750,811

(22) Filed: Mar. 31, 2010

(65) Prior Publication Data

US 2011/0242539 A1  Oct. 6, 2011

(51) Int. Cl.
G01N 21/00 (2006.01)

(52) U.S. Cl. .................... 356/436; 356/440

(58) Field of Classification Search ........... 356/436–444
See application file for complete search history.

(56) References Cited

U.S. PATENT DOCUMENTS

| | | | |
|---|---|---|---|
| 3,988,591 A | 10/1976 | Killer | |
| 4,295,199 A | 10/1981 | Curry | |
| 4,783,314 A | 11/1988 | Hoots et al. | |
| 5,872,361 A * | 2/1999 | Paoli et al. | 250/341.8 |
| 6,255,118 B1 | 7/2001 | Alfano et al. | |
| 6,369,894 B1 | 4/2002 | Rasimas et al. | |
| 6,831,745 B2 | 12/2004 | Marquardt et al. | |
| 6,842,243 B2 | 1/2005 | Tokhtuev et al. | |
| 6,977,729 B2 | 12/2005 | Marquardt et al. | |
| 7,095,500 B2 | 8/2006 | Banks | |
| 7,154,603 B2 | 12/2006 | Banks | |
| 7,173,244 B2 * | 2/2007 | Tomita et al. | 250/336.1 |
| 7,179,384 B2 | 2/2007 | Moriarty et al. | |
| 7,198,755 B2 | 4/2007 | Tokhtuev et al. | |
| 7,220,382 B2 | 5/2007 | Godfrey et al. | |
| 7,242,001 B1 | 7/2007 | Hedges et al. | |
| 7,550,746 B2 | 6/2009 | Tokhtuev et al. | |
| 7,652,267 B2 * | 1/2010 | Tokhtuev et al. | 250/461.1 |
| 2005/0229698 A1 | 10/2005 | Beecroft et al. | |
| 2006/0246595 A1 | 11/2006 | Banks et al. | |
| 2009/0150106 A1 | 6/2009 | Erickson et al. | |
| 2009/0212236 A1 | 8/2009 | Tokhtuev et al. | |

(Continued)

FOREIGN PATENT DOCUMENTS

JP  05072131 A  3/1993

(Continued)

OTHER PUBLICATIONS

International Search Report and Written Opinion, PCT/IB2011/051346, Aug. 25, 2011, 8 pages.

(Continued)

*Primary Examiner* — Michael P Stafira
(74) *Attorney, Agent, or Firm* — Fredrikson & Byron, PA

(57) ABSTRACT

Embodiments provide a handheld optical measuring device and method of measuring an optical property of a liquid sample. In some embodiments the optical measuring device includes a handheld controller module having an immersible sensor head and a sampling member including a sample cup and an attachment member that couples the sample cup to the handheld controller module. In some embodiments the attachment member is an elongated rigid member that is hingedly coupled to the controller module, thus providing a folding configuration for enclosing the sensor head with the sample cup during measurements, transportation, and/or storage. In some embodiments the attached sample cup provides a protective shell for the immersible sensor head during use and/or when not in use.

22 Claims, 12 Drawing Sheets

U.S. PATENT DOCUMENTS

| | | |
|---|---|---|
| 2009/0283698 A1 | 11/2009 | Chapman |
| 2010/0120016 A1* | 5/2010 | Li et al. .............................. 435/5 |
| 2010/0231904 A1* | 9/2010 | Tyrie et al. .................... 356/319 |

FOREIGN PATENT DOCUMENTS

| | | |
|---|---|---|
| JP | 08313533 A | 11/1996 |
| WO | WO2007064820 A3 | 6/2007 |
| WO | 2007143047 A1 | 12/2007 |

OTHER PUBLICATIONS

English Abstract for JP 08313533 (A), published Nov. 29, 1996, Daikin Ind. Ltd., 1 page.

English Abstract for JP 05072131 (A), published Mar. 23, 1993, Kurita Water Ind. Ltd., 1 page.

Turner Designs, Aquafluor Handheld Flurometer and Turbidimeter User's Manual, Sep. 2004, Version 1.3, pp. 1-36.

Nalco, Traced Antiscalant Control with RO-TRASAR, http://www.extranet.nalco.com/ASP/applications/membrane_tech/equipment/ro_trasar.asp, pp. 1-2.

Turner BioSystems, Picofluor Handheld Fluorometer Operating Manual, Feb. 2010, Version 1.5, pp. 1-16.

Issue Fee Transmittal Documents for U.S. Appl. No. 12/750,922, transmitted Jun. 21, 2012, 4 pages.

* cited by examiner

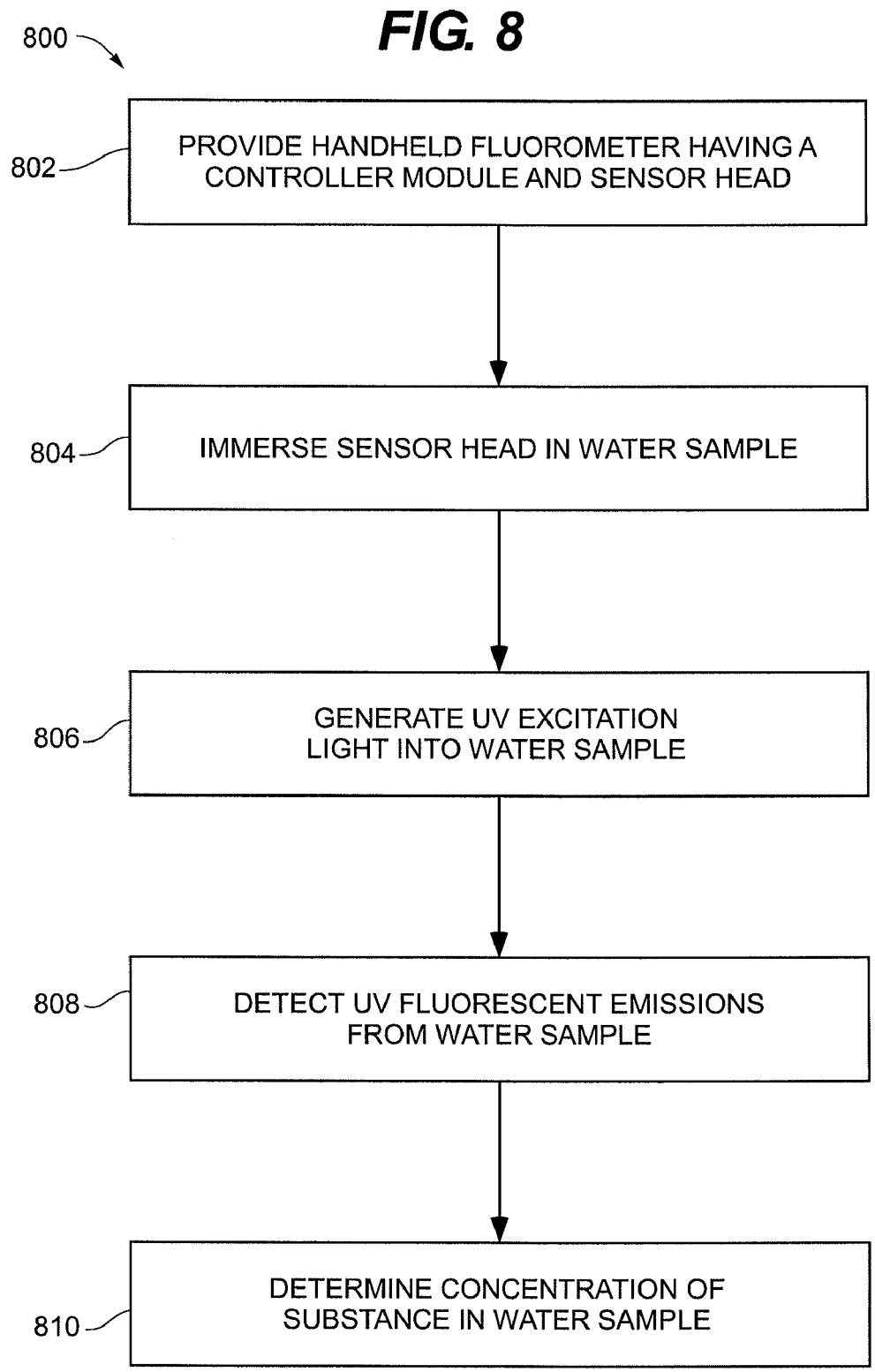

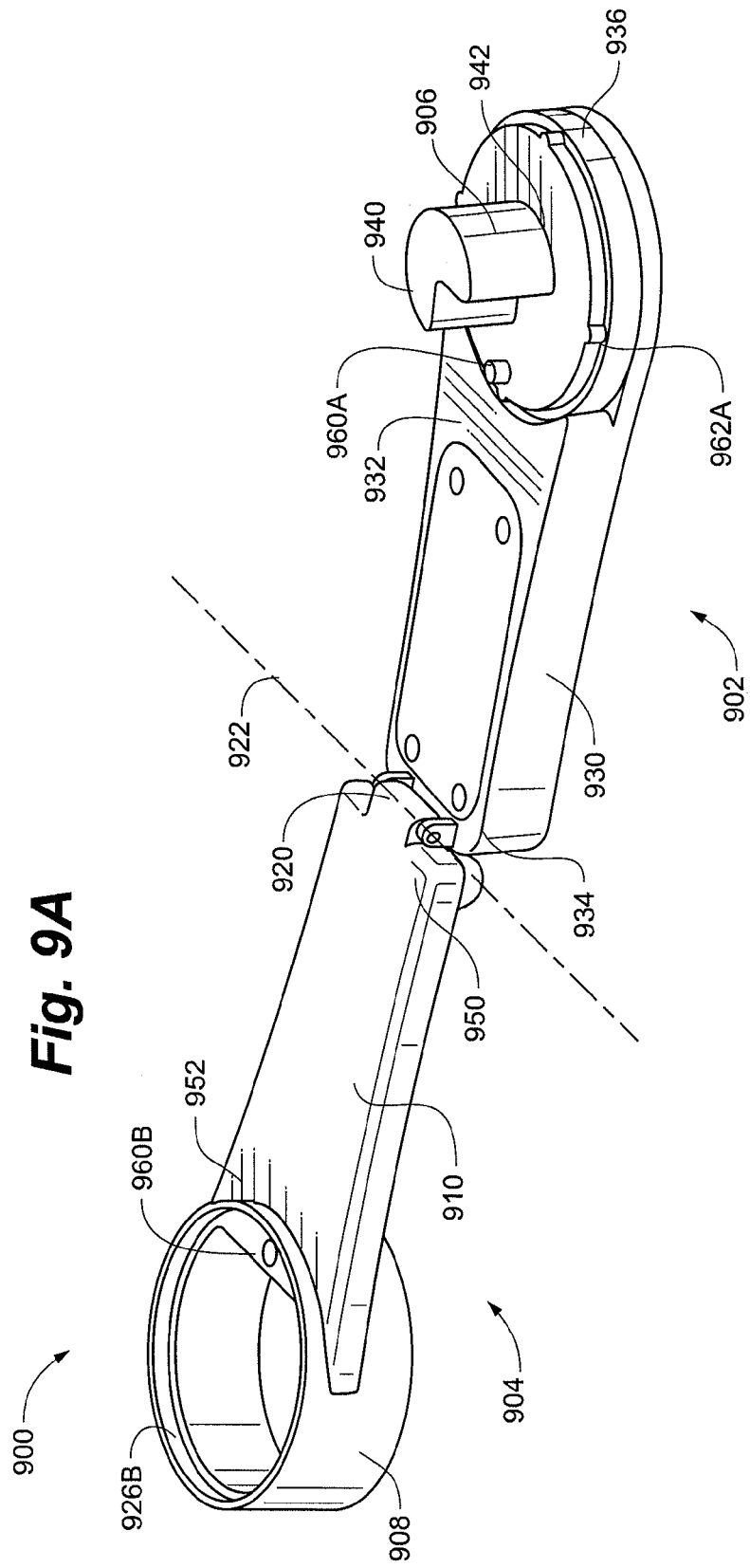

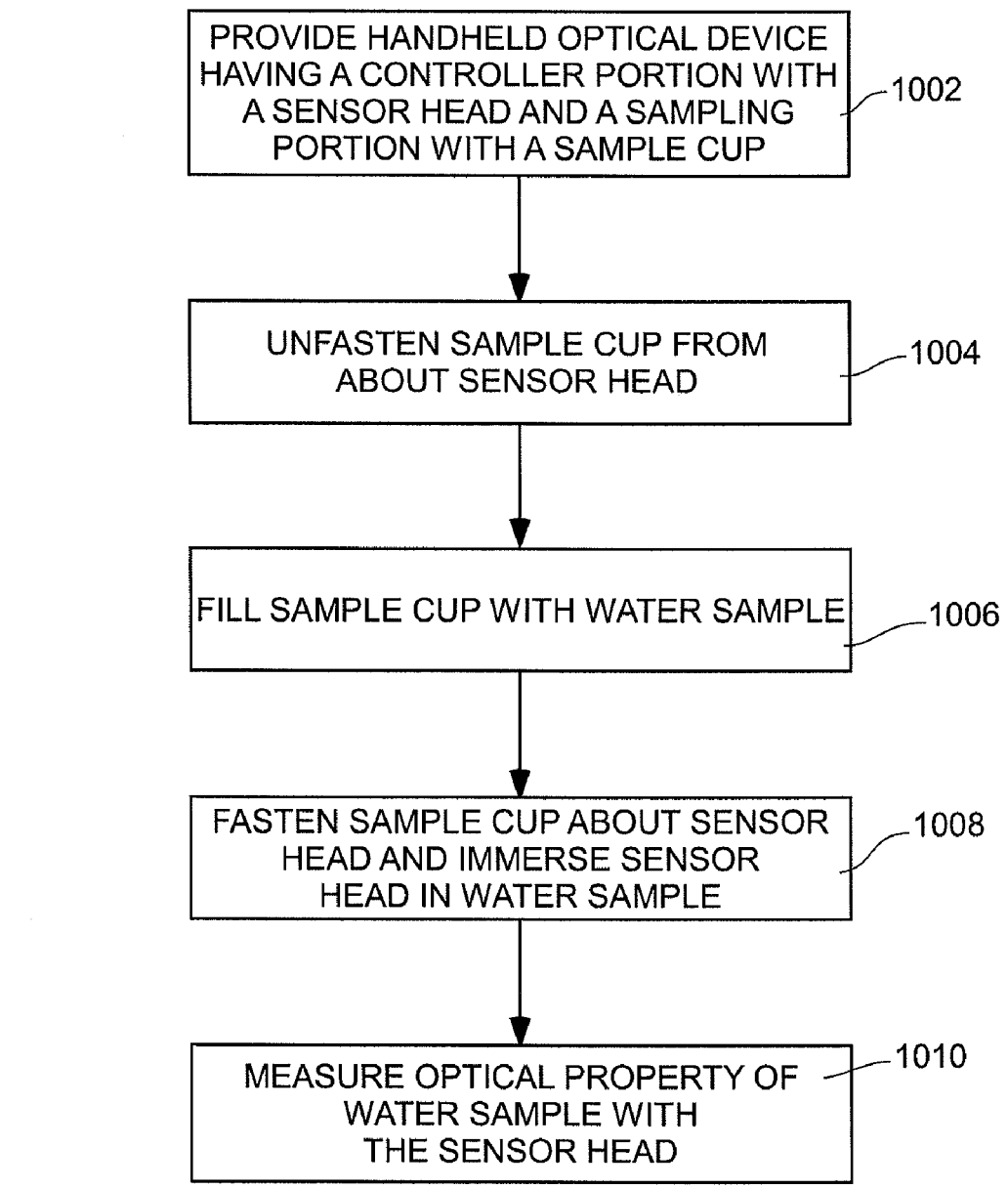

HANDHELD OPTICAL MEASURING DEVICE AND METHOD OF USE

BACKGROUND

Embodiments of the present invention generally relate to optical measuring devices for testing a liquid sample, and more particularly to handheld optical measuring devices having immersible sensors for measuring one or more optical properties of a liquid sample.

Monitoring water quality, including various substances within a water sample, is a process widely used in many fields, and as will be appreciated, can be important in any application that relies on maintaining and/or changing various characteristics of a water sample. Some examples of relevant applications include monitoring natural water sources for environmental concerns, monitoring industrial water systems to ensure adequate performance, and monitoring municipal water systems to ensure quality criteria are met. Of the countless ways to test, characterize, and monitor water flows, measuring the optical properties of a water sample has become an important and reliable method for characterizing certain properties of the water sample. A number of methods are available for measuring the optical properties of a water sample.

Absorption spectroscopy can provide information about the range of electromagnetic spectra absorbed by one or more substances in a water sample. In using a spectrophotometer, ultraviolet and/or visible light at a certain wavelength (or range of wavelengths) is shined through the water sample. The spectrophotometer measures how much of the light is absorbed by the water sample. The concentration of the substance in a water sample can then be determined by measuring the intensity of the light transmitted through the water sample and calculating the concentration of the substance based on the measured water sample transmission.

Fluorometric spectroscopy concerns the detection of fluorescent light emitted by a sample of interest. It involves using a beam of light, usually ultraviolet (UV) light, that excites the electrons in molecules of certain compounds in the sample and causes them to emit light of a lower energy (i.e., to "fluoresce"). There are several types of fluorometers for measuring emitted fluorescence. Fluorometers generally have of a source of excitation radiant energy, an excitation wavelength selector, a sample cell to contain the sample material, an emission wavelength selector, a detector with signal processor and a readout device. Filter fluorometers use optical filters to isolate the incident light and fluorescent light. Spectrofluorometers use diffraction grating monochromators to isolate the incident light and fluorescent light.

One method of monitoring the concentration of a chemical product (e.g., a cleaning agent) within a water sample relies on monitoring the fluorescence of the product that occurs when the sample (and the product within the sample) is exposed to a predetermined wavelength of light. For example, compounds within the product or a fluorescent tracer added to the product may fluoresce when exposed to certain wavelengths of light. The concentration of the product can then be determined using a fluorometer that measures the fluorescence of the compounds and calculates the concentration of the chemical based on the measured fluorescence. Such determinations can be especially important in cleaning and antimicrobial operations in which commercial users (e.g., restaurants, hotels, food and beverage plants, grocery stores, etc.) rely upon the concentration of the cleaning or antimicrobial product to make the product work effectively. The same may be true for other applications, such as water care, pest control, beverage and bottling operations, packaging operations, and the like.

Turbidity sensing provides a quick, practical indication of the relative amount of suspended solids in water or suspended liquids. Many industrial and commercial bath applications can make use of turbidity and conductivity sensing to improve product quality, minimize ingredient consumption, and reduce wastewater discharge. Turbidity sensors often determine the amount of suspended solids based on the amount of light transmitted through a sample or scattered by a sample.

Other methods of measuring and monitoring optical properties of a water sample are also available.

SUMMARY

Embodiments of the invention generally relate to various designs for a handheld optical measuring device having an integral sample cup and an immersible sensor head capable of measuring one or more properties of a water sample within the cup with the sensor head is immersed in the water sample. Embodiments of the handheld device are advantageously self-contained and incorporate components that allow the handheld optical device to contain a water sample away from the water source and measure and display characteristics of the water sample to a user without the need for communication with exterior equipment.

According to one aspect of the invention, a handheld optical measuring device is provided including a handheld controller module and a sampling member. The controller module is adapted (e.g., sized and shaped) to be held by a user's hand, and includes a housing having a bottom surface. A controller is positioned within the housing for calculating an optical property of a water sample based on an optical sensor signal. The controller module also includes an immersible sensor head having a housing with a proximal end and a distal end, wherein the sensor head is connected to the bottom surface of the controller module housing at the proximal end of the sensor head housing. The controller module further includes at least one optical sensor coupled to the controller that is able to generate and transmit the optical sensor signal to the controller based on the optical property of the water sample when the sensor head is immersed in the water sample. The sampling member generally includes a sample cup and an attachment member coupled to the sample cup and the handheld controller module for retaining the sample cup with the handheld controller module. The sample cup contains the water sample and is removably fastenable about the sensor head such that the water sample can be introduced into the sample cup when the sample cup is not fastened about the sensor head. When the sample cup containing the water sample is fastened about the sensor head, at least a portion of the sensor head is immersed in the water sample. The attachment member can retain the sample cup with the handheld controller module whether or not the sample cup is fastened about the sensor head.

According to another aspect of the invention, a handheld optical measuring device is provided having a controller portion, a sampling portion, and a pivot coupling the controller portion and the sampling portion. The controller portion includes an elongated rigid housing with a bottom surface, and a first end and a second end between which extends a length of the controller portion housing. The controller portion also includes a controller adapted to calculate an optical property of a water sample based on an optical sensor signal and an immersible sensor head having at least one optical sensor coupled to the controller. The optical sensor has a proximal end and a distal end between which extends a length of the sensor head, and the proximal end of the sensor head is connected to the bottom surface of the controller portion housing proximate to the first end of the controller portion housing. The sampling portion includes an elongated rigid attachment member with a first end and second end between which extends a length of the attachment member. The pivot couples the second end of the attachment member to the second end of the controller portion housing and the first end of the attachment member is coupled to a sample cup for receiving the water sample. The sample cup is removably fastenable about the sensor head such that the sensor head is at least partially immersed in the water sample contained in the sample cup with the sample cup fastened about the sensor head.

According to another aspect of the invention, a method for measuring an optical property of a water sample is provided. The method includes providing a handheld optical measuring device having a controller portion with an immersible sensor head, and a sampling portion with a sample cup and an attachment member coupling the sample cup to the controller portion. The sample cup is preferably removably fastenable about the sensor head. The method also includes unfastening the sample cup from about the sensor head, introducing a water sample into the sample cup, and fastening the sample cup about the sensor head such that at least part of the sensor head is immersed in the water sample. The sample cup preferably remains coupled to the attachment member and the controller portion whether or not it is fastened about the sensor head. Once the sensor head is immersed in the water sample, the method also includes measuring an optical property of the water sample with the sensor head and the controller portion.

Embodiments of the present invention can provide one or more of the following features and/or advantages. Some embodiments provide improved protection for an immersible dip probe and associated optics during measurements and/or during storage and transportation. In some embodiments an attached sample cup provides a protective shell for the immersible sensor head during use and/or when not in use. In some cases the handheld optical measuring device includes a cavity for containing a water sample and another cavity for containing overfill spills during measurements. In some embodiments a protective shell can be permanently attached to the housing of the handheld optical device, adding convenience in field use. The protective shell can provide an extended handle, making it easier to grab or scoop a water sample from an open body of water. In some embodiments the attached nature of the sample cup can allow measurements of the scooped sample with minimal delay and without additional preparation or handling steps.

These and various other features and advantages will be apparent from a reading of the following detailed description.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

FIG. 8 is a flow diagram depicting a method for determining a concentration of a substance in a water sample according to some embodiments of the invention.

FIG. 9A is a perspective view of an optical measuring device in an open position according to some embodiments of the invention.

FIG. 10 is a flow diagram depicting a method for measuring an optical property of a water sample according to some embodiments of the invention.

DETAILED DESCRIPTION OF THE PREFERRED EMBODIMENTS

The following detailed description is exemplary in nature and is not intended to limit the scope, applicability, or configuration of the invention in any way. Rather, the following description provides some practical illustrations for implementing exemplary embodiments of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Embodiments of the invention generally provide a handheld optical measuring device having an immersible sensor head and methods of using such a device. Components of the handheld optical measuring device are advantageously self-contained in a handheld configuration, providing a convenient tool for a variety of uses. In some embodiments of the invention, an optical measuring device in the form of a handheld fluorometer is provided. While some embodiments of the invention are described herein with reference to a handheld fluorometer, it should be understood that aspects of the invention can be embodied in a variety of optical measuring devices (e.g., turbidimeter, optical absorbance meter, etc.) and the invention is not limited to any particular form of device.

Figure 1:
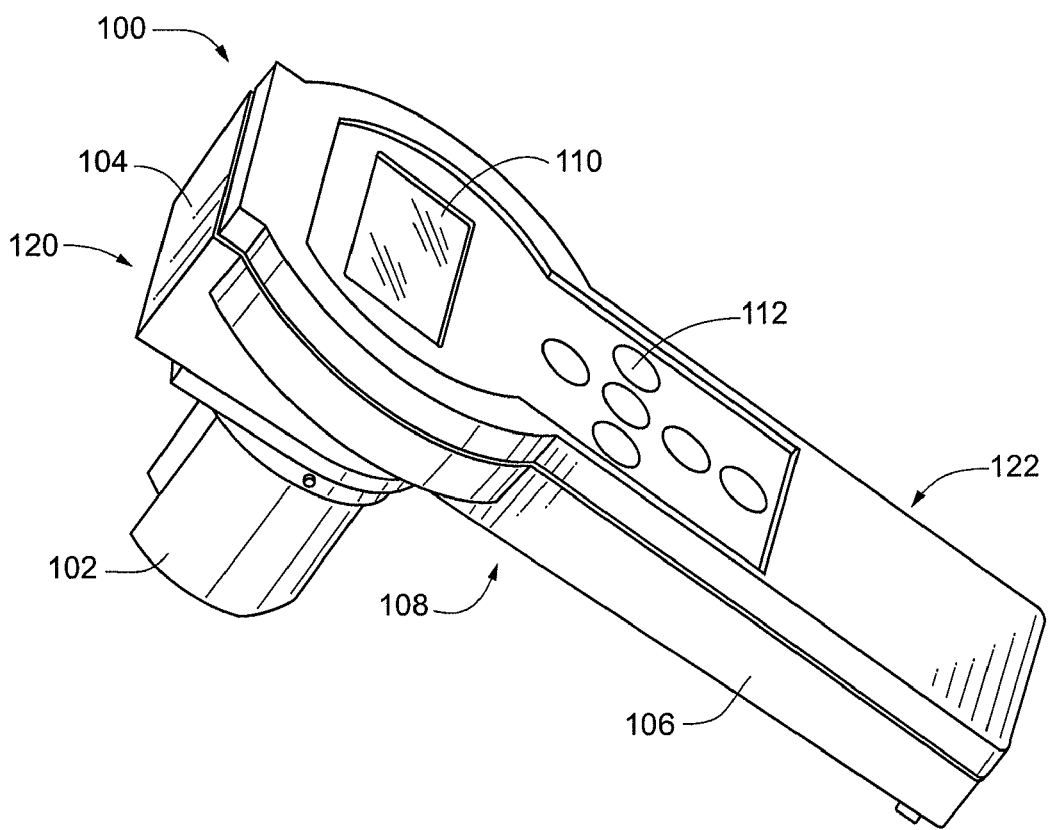
FIG. 1 is a perspective view of a handheld fluorometer according to some embodiments of the invention.

FIG. 1 is a perspective view of an optical measuring device in the form of a handheld fluorometer 100 according to some embodiments of the invention. The fluorometer 100 generally includes an immersible sensor head 102 connected to a handheld controller module 104. The controller module 104 also includes an electronic display 110 for displaying sensor readings and calculations to a user, and an input interface in the form of a keypad 112 that allows the user to interact with the fluorometer 100 (e.g., entering variables, setting parameters, accessing menu items, etc.).

According to some embodiments, the controller module 104 has a generally elongated housing 106 which provides a convenient form, similar to a handle or wand, to easily grasp or hold the fluorometer 100 by the hand. The sensor head 102 preferably includes a water-tight housing that enables it to take measurements and otherwise function when partially or wholly immersed in a liquid sample of interest. Accordingly, in some cases the sensor head 102 has some features and/or characteristics similar to an immersible dip probe. For example, in some embodiments of the invention the immersible sensor head 102 has one or more features and/or components similar to those described in commonly-assigned U.S. Pat. No. 7,550,746 and U.S. Patent Application Publication 2009/0212236, the entire contents of each of which is hereby incorporated herein by reference. The configuration of the immersible sensor head 102 can also be contrasted in some ways with fluorometers and other optical instruments that position sensors and other components exterior to an optical cell containing the sample of interest.

In some cases the sensor head 102 is connected to (e.g., attached to or integral with) a bottom surface 108 of the controller housing 106 opposite from the display 110 and positioned proximate a distal end 120 of the controller housing. In a typical fashion, a user can grasp the controller housing 106 near a proximal end 122 of the controller housing to take measurements from a sample, read the display 110, and/or manipulate the keypad 112. For example, a user may dip the sensor head 102 into a sample by holding the controller module 104 above the surface of a liquid sample (e.g., in a reservoir/container in the field, a beaker in the laboratory, etc.) with the sensor head 102 partially or completely immersed in the sample. In some embodiments, a user may grasp the second end of the controller module 104 while securing a sample cup filled with a sample about the immersible sensor head 102. Of course other configurations of the controller module and the sensor head are possible and the invention is not limited to any particular physical configuration.

In general, the handheld fluorometer 100 at minimum measures fluorescent emissions from a sample including a substance of interest (e.g., a chemical solution, such as an antimicrobial or cleaning product), calculates a concentration of the substance in the sample, and displays the determined concentration to a user. The user can then optionally perform any desired actions based on the determined concentration, such as, for example, adding more of the substance to an industrial system in order to increase the concentration of the substance. In this way, the fluorometer can be part of a manual feedback loop. If the fluorometer determines that the concentration is lower or higher than a threshold concentration, a user will see the difference and can adjust the product dispensation appropriately by either dispensing more or less product. Additionally, the fluorometer can function as part of an out-of-product alarm. When a product runs out, the fluorescence (which reflects the concentration of the product) will drop below a pre-determined threshold level. At this point, the sensor can alert a user that the dispenser is out of product. The signal can be a visual or audio signal, or a vibrating signal. Accordingly, such feedback will ensure that enough cleaner, antimicrobial or other composition is present to achieve the desired effect (cleanliness, reduction in microorganisms, lubrication, etc.).

The basic operation of fluorometers is well known, and accordingly, various details are omitted here for conciseness and clarity. In general, the fluorometer 100 calculates a concentration of a particular substance in a liquid sample based on fluorescent properties of the substance. As will be described in more detail herein, the fluorometer 100 includes a light source that emits light within a selected wavelength range. When the sensor head 102 is immersed in the liquid sample, the light encounters particles of the substance of interest, which excites the electrons in certain molecules of the substance and causes them to emit light of a lower energy (i.e., to "fluoresce") in another wavelength range. The sensor head 102 includes an optical sensor, such as a photodetector, that detects the fluorescent emissions and generates a corresponding electrical signal indicating the intensity of the fluorescent emissions. The fluorometer 100 includes a controller, coupled with the optical sensor, that can then calculate the concentration of the substance based on a known relationship between the intensity of the fluorescent emissions and the concentration of the substance.

A number of variations and specific details of this general process are contemplated for embodiments of the invention involving fluorometers. For example, the substance of interest may be any desired chemical solution having fluorescent properties. Examples include, but are not limited to, biocides such as pesticide and antimicrobial products, anticorrosion, antiscaling, and antifouling products, disinfectants, and other cleaning products, detergents, additives, and the like. For convenience, these and other such substances are alternately referred to herein simply as "products," "chemical solutions," and/or "treatment solutions." In addition, although examples are presented herein involving determining the concentration of water treatment solution(s) within a sample of cooling water (e.g., a water sample) used in various industrial systems (e.g., a cooling tower), it should be appreciated that the handheld fluorometer 100 may be useful in determining the concentration(s) of products used in numerous settings to treat water and other liquids. As just a few examples, the handheld fluorometer 100 may be useful for determining concentrations of one or more substances in laundry, automatic ware-washing, manual ware-washing, $3^{rd}$ sink applications, power sink applications, vehicle care, clean-in-place operations, healthcare applications, hard surface applications and the like.

Many products fluoresce in the presence of light radiating from the sensor head 102 because many of the compounds that make up the products have fluorescent characteristics. For example, a compound or molecule that has a benzene component can incorporate one or more substituent electron donating groups such as —OH, —$NH_2$, and —$OCH_3$, and polycyclic compounds that exhibit fluorescent characteristics. Many compounds used in the above-described applications include chemical structures like these, such as surfactants, lubricants, antimicrobial agents, solvents, hydrotropes, antiredeposition agents, dyes, corrosion inhibitors and bleaching additives. These compounds can be incorporated into products like ware-washing detergents, rinse aids, laundry detergents, clean-in-place cleaners, antimicrobials, floor coatings, meat, poultry and seafood carcass treatments, pesticides, vehicle care compositions, water care compositions, pool and spa compositions, aseptic packaging compositions, bottle washing compositions, and the like. Examples of some of these compounds and corresponding applications can be found in U.S. Pat. No. 7,550,746, the entire content of which is herein incorporated by reference.

Additionally, or alternatively, fluorescent tracers (also referred to herein as "fluorescent markers") can be incorporated into products that may or may not already include naturally fluorescing compounds. Some non-limiting examples of tracers include naphthalene disulfonate (NDSA), 2-naphthalenesulfonic acid, Acid Yellow 7,1,3,6,8-pyrenetetrasulfonic acid sodium salt, and fluorescein. In some embodiments the fluorescent tracer is added to the product in a known proportion, thus making it possible to estimate the concentration of the product once the concentration of the tracer is determined. For example, in some cases the concentration of the fluorescent tracer can be determined by comparing a current fluorescent signal with fluorescent signals from known tracer concentrations measured during a calibration procedure. The concentration of chemical product can then be estimated from the known nominal proportion of fluorescent tracer and measured concentration of fluorescent tracer. In some cases a current concentration of a product, $C_c$, in a liquid sample can be determined by $$C_c = C_m \times (C_0/C_f), \text{ wherein}$$

$$C_m = K_m \times (S_x - Z_0), \text{ and}$$

wherein $C_m$ is a current fluorescent marker concentration, $K_m$ is a slope correction coefficient, $S_x$ is a current fluorescent measurement, $Z_0$ is a zero shift, $C_0$ is a nominal concentration of the product, and $C_f$ is a nominal concentration of the fluorescent tracer.

Figure 2:
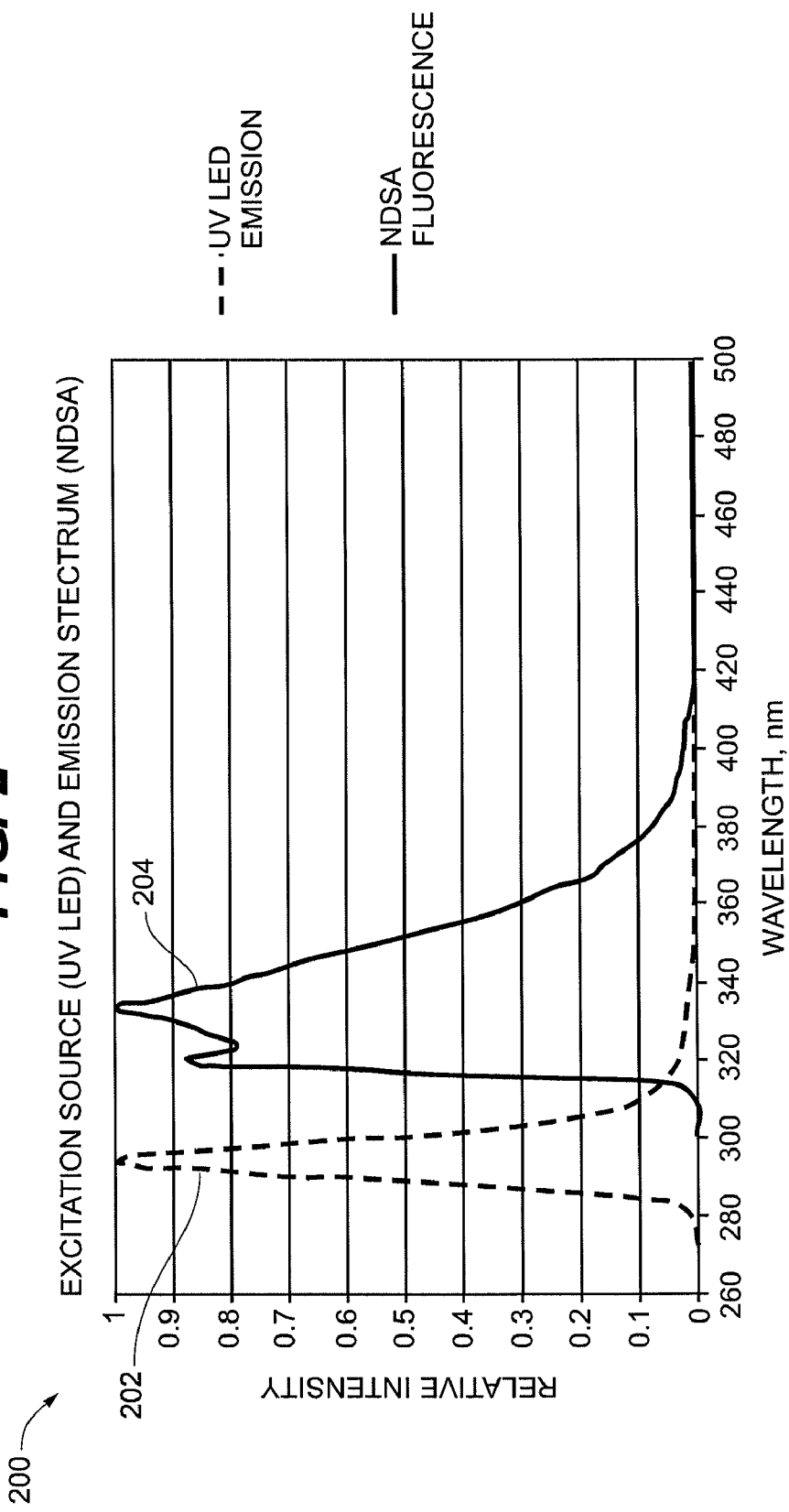
FIG. 2 is a plot of excitation and emission spectrum intensity according to some embodiments of the invention.

Referring to FIG. 2, a plot 200 is shown of an excitation spectrum intensity 202 and an emission spectrum intensity 204 according to some embodiments of the invention. In this example, a fluorometer having a light source in the form of an ultra violet (UV) light emitting diode (LED) emits excitation light within a range from about 280 nm to about 310 nm into a sample of cooling tower water having a product with an added fluorescent tracer, NDSA. The added NDSA absorbs this UV radiation and produces fluorescence in a range from about 310 nm to about 400 nm. The emission detector of the fluorometer detects this emitted radiation, and the fluorometer determines the concentration of the NDSA tracer, and ultimately the concentration of the product within the sample of the cooling tower water.

Figure 3:
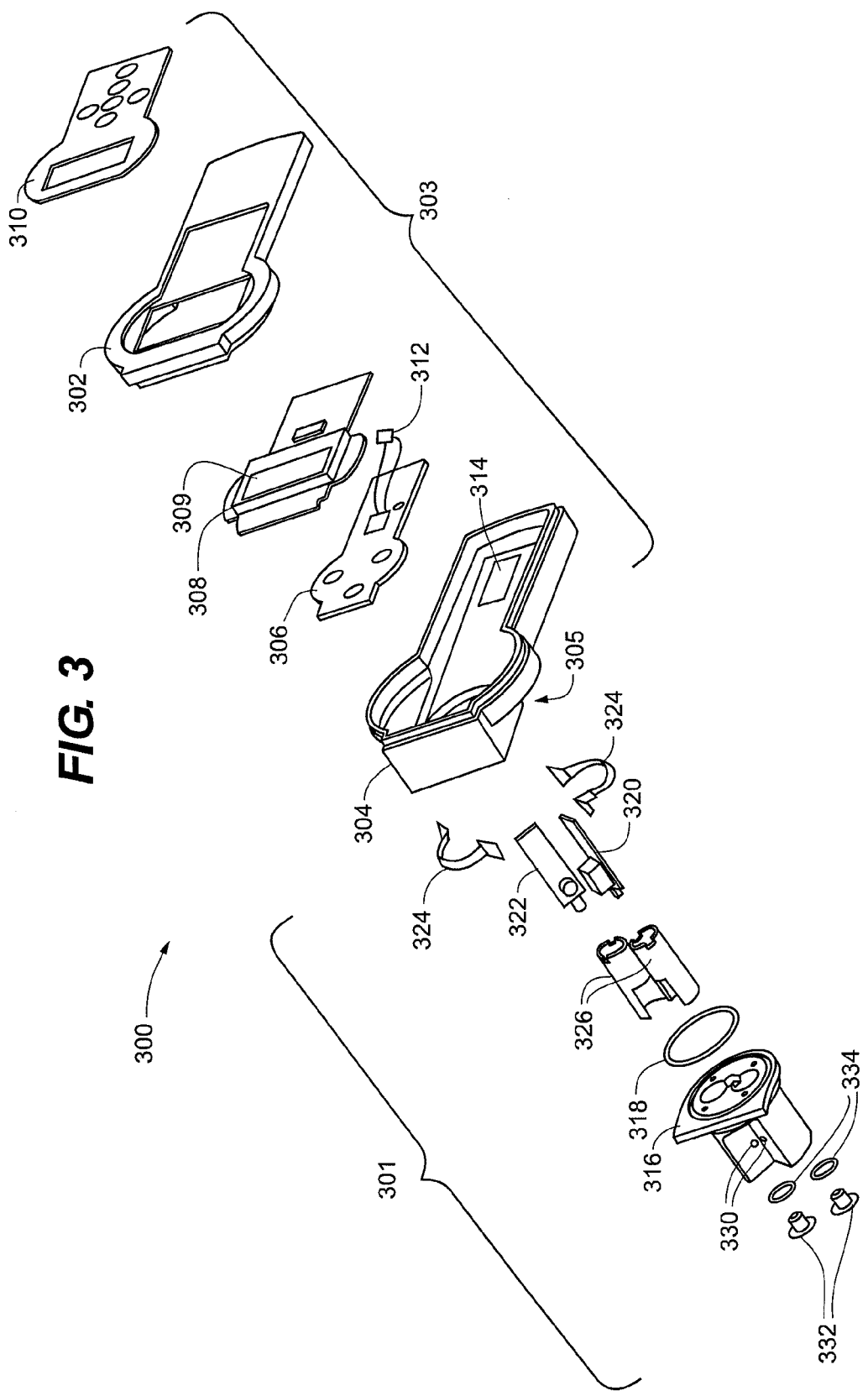
FIG. 3 is an exploded view of a handheld fluorometer according to some embodiments of the invention.

FIG. 3 is an exploded view of a handheld fluorometer 300 similar to the handheld fluorometer shown in FIG. 1. The fluorometer 300 generally includes an immersible sensor head 301 connected to a controller module portion 303. The controller module 303 includes a housing and several components within the housing. The housing is formed from a top portion 302 and a bottom portion 304, with the bottom portion 304 of the controller housing defining a bottom surface 305 on the exterior of the bottom portion. The sensor head 301 includes a sensor head housing 316 that is configured to be fixedly attached to the bottom surface 305 of the controller housing. In some embodiments the sensor head housing 316 may be integrally formed with one or more portions of the controller housing.

In some embodiments the controller module 303 generally includes those components necessary to determine a concentration of a product based on a signal received from the sensor head 301. As shown in FIG. 3, the controller module 303 includes a control board 306 that couples with a display board 308 via a display board cable 312. The display board 308 includes an electronic display 309 (e.g., an LCD screen) that displays information to a user. The controller module 303 also includes an input interface in the form of a membrane keypad overlay 310, which allows the user to enter a variety of information for use by the controller module 303. The controller module 303 also includes a portable power source, e.g., battery, 314 for powering the circuits within the fluorometer 300.

In some embodiments the immersible sensor head 301 has one or more features and/or components similar to those described in commonly-assigned U.S. Pat. No. 7,550,746 and U.S. Patent Application Publication 2009/0212236, the entire contents of each of which is hereby incorporated herein by reference. Referring back to FIG. 3, in some embodiments, the sensor head 301 includes a housing 316 that houses a light source board 320 and an emission detector board 322. A first O-ring 318 provides a seal between the sensor head housing 316 and the bottom portion 304 of the controller housing. The components on the light source board 320 and the emission detector board 322 are shielded by a brass tube 326 that substantially encircle each board. Each tube 326 includes a cutout at the distal end of the tube, and the sensor head housing 316 includes windows 330 extending through the housing. These cutouts and the windows 330 allow a light source (e.g., LED) positioned on the light source board 320 and an emission detector (e.g., photodetector) positioned on the emission detector board 322 to communication with an analytical area outside the sensor head housing 316. Electrical cables 324 couple the light source board 320 and the emission detector board 322 to the control board 306, which allows the controller on the board 306 to control the light source and receive signals back from the emission detector. In some embodiments the sensor head 301 also includes one or more temperature sensors that are able to measure the temperature of a water sample. For example, the light source board 320 and/or the emission detector board 322 may include one or more temperature sensors that extend into the sensor head housing 316. Covers 332 positioned in a distal face of the sensor housing 316, along with additional O-rings 334, provide a seal around the temperature sensors.

Figure 4:
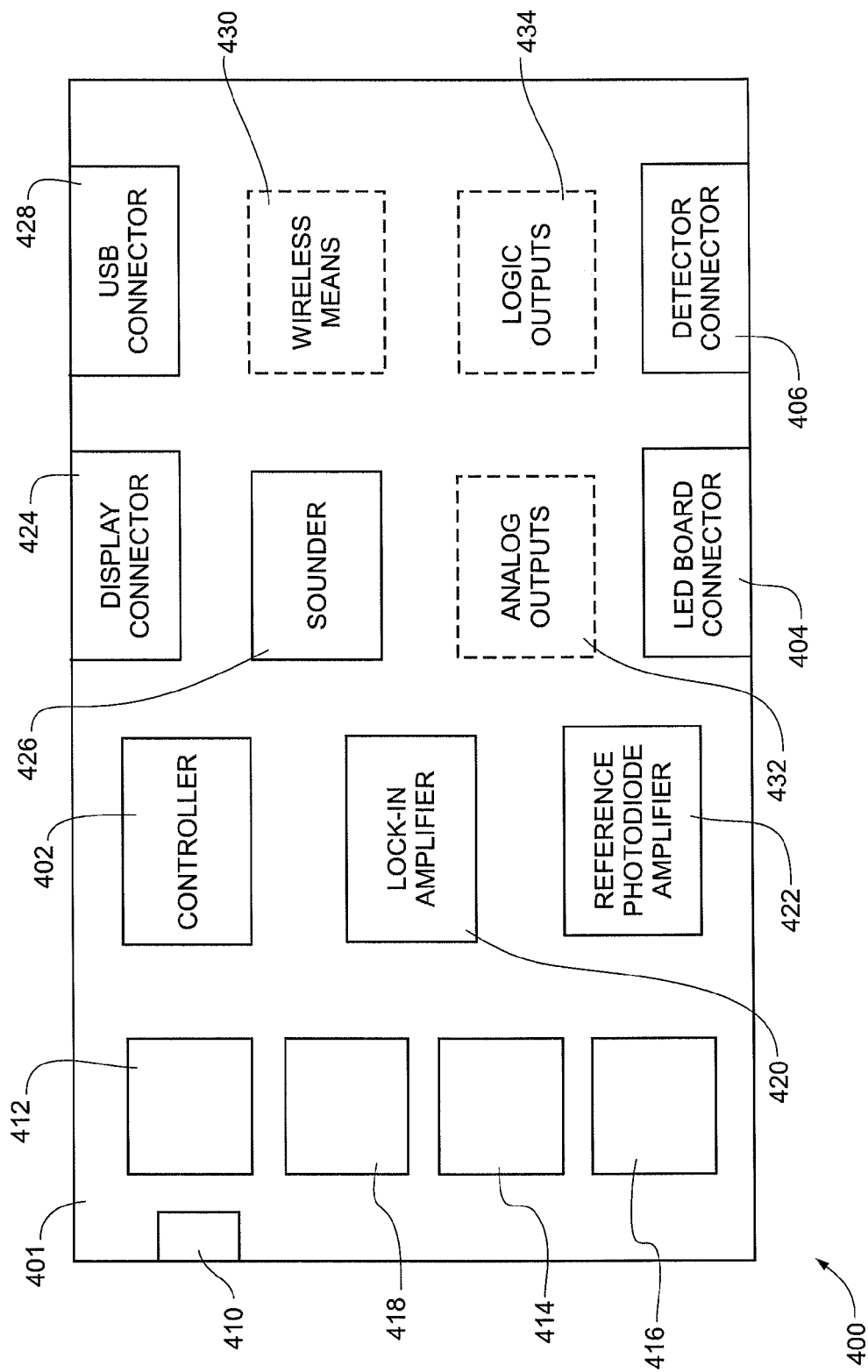
FIG. 4 is a schematic diagram of a controller board according to some embodiments of the invention.

FIG. 4 is a schematic diagram of a controller board 400 for a handheld fluorometer according to some embodiments of the invention. The controller board 400 can comprise a number of discrete components positioned (e.g., soldered) and coupled together (connections not shown) on a printed circuit board 401. FIG. 4 presents a simplified schematic of the basic components of one exemplary control board 400, and it will be appreciated by those skilled in the art that various connections between the components and/or details about components may vary. The control board 400 includes a controller 402, which calculates a concentration of a product within a water sample based on an intensity signal from the emission detector. The controller 402 may provide a variety of other functions, including without limitation, performing a calibration routine, accepting and executing instructions entered at the input interface, and/or formatting data for viewing on the fluorometer's display. The controller 402 can be embodied in any suitable form, such as a software driven microprocessor, a microcontroller, or a field programmable gate array, or a fixed hardware design such as an application specific integrated circuit, etc. In addition, the controller 402 may have onboard memory, or the control board may have memory (not shown) that stores instructions for execution by the controller 402.

The control board also includes a power cable with a connector 410 for connecting the board 400 to a power source such as the battery 314 shown in FIG. 3. The board 400 also includes a controller power supply 412, an analog power supply 414, and a light source power supply 416 for powering the light source in the sensor head. In some embodiments the control board 400 includes a real-time clock battery 418, a lock-in amplifier 420, a reference photodiode amplifier 422, and connectors for the display board 424, the light source board 404, and the emission detector board 406. In some cases, the control board 400 may also have a sounder 426, a USB or other type of data connector 428, wireless means 430 for communicating with other computing devices, and optional analog 432 and logical 434 outputs.

Figure 5:
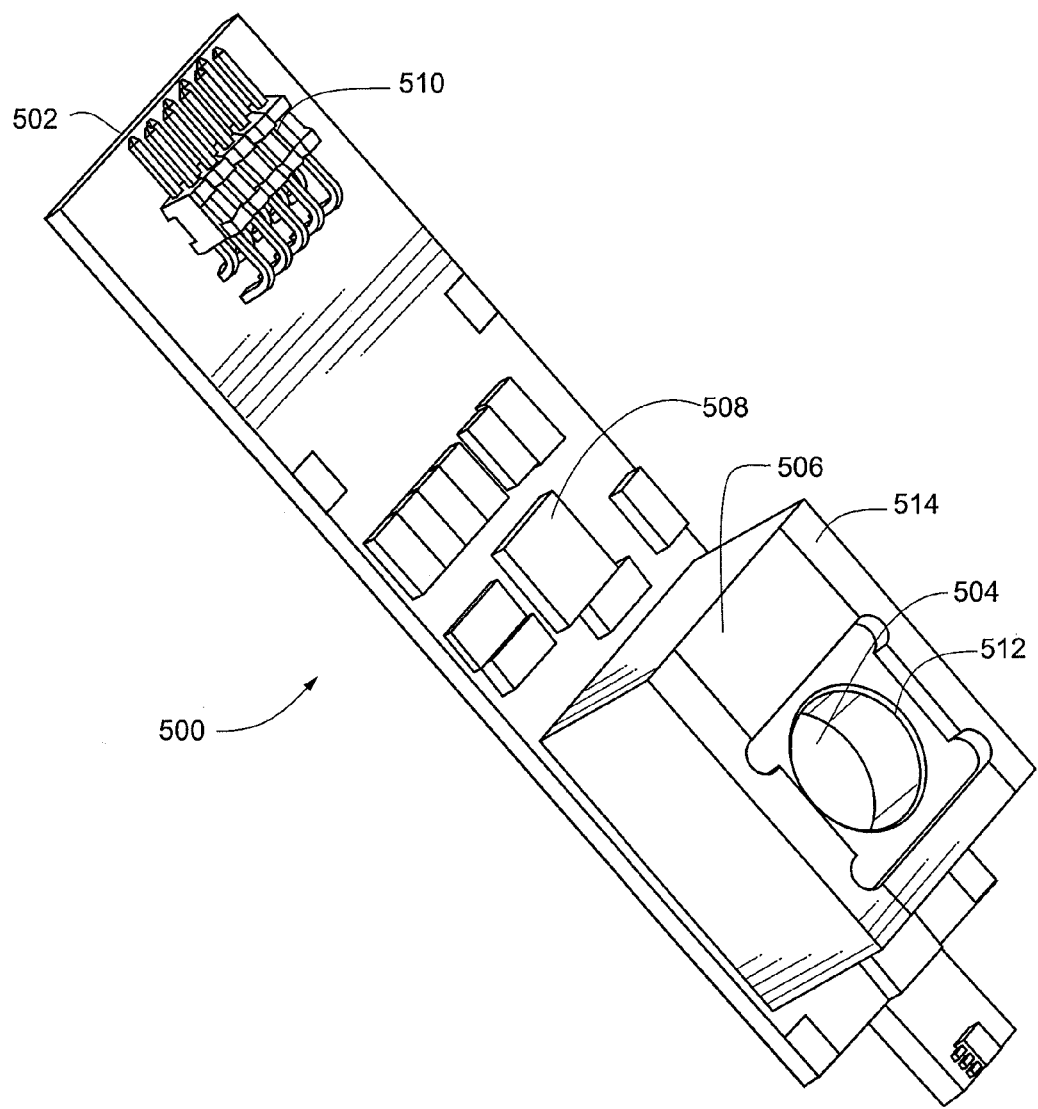
FIG. 5 is a perspective view of a light source board according to some embodiments of the invention.

FIG. 5 is a perspective view of a light source board 500 according to some embodiments of the invention. The board 500 (also shown in FIG. 3 as 320) generally includes a printed circuit board 502 having a light source 504 and a reference photodiode 506, along with a preamplifier 508 and a connector 510 for coupling the board 500 with the control board. An excitation filter 512 is positioned by a filter holder 514 over the light source 504, to filter the light from the light source 504 before it leaves the immersible sensor head. The light source 504 can include a variety of possible elements. For example, light source 504 may be a gas discharge lamp, a mercury lamp, a deuterium lamp, a metal vapor lamp, a light emitting diode (LED) or a plurality of LEDS. In addition, the light source 504 may emit excitation radiation in a number of possible spectrums depending upon the element chosen and the spectrum desired. In some embodiments the light source is an ultraviolet LED, capable of emitting light having a wavelength from about 280 nm to about 310 nm.

Figure 6:
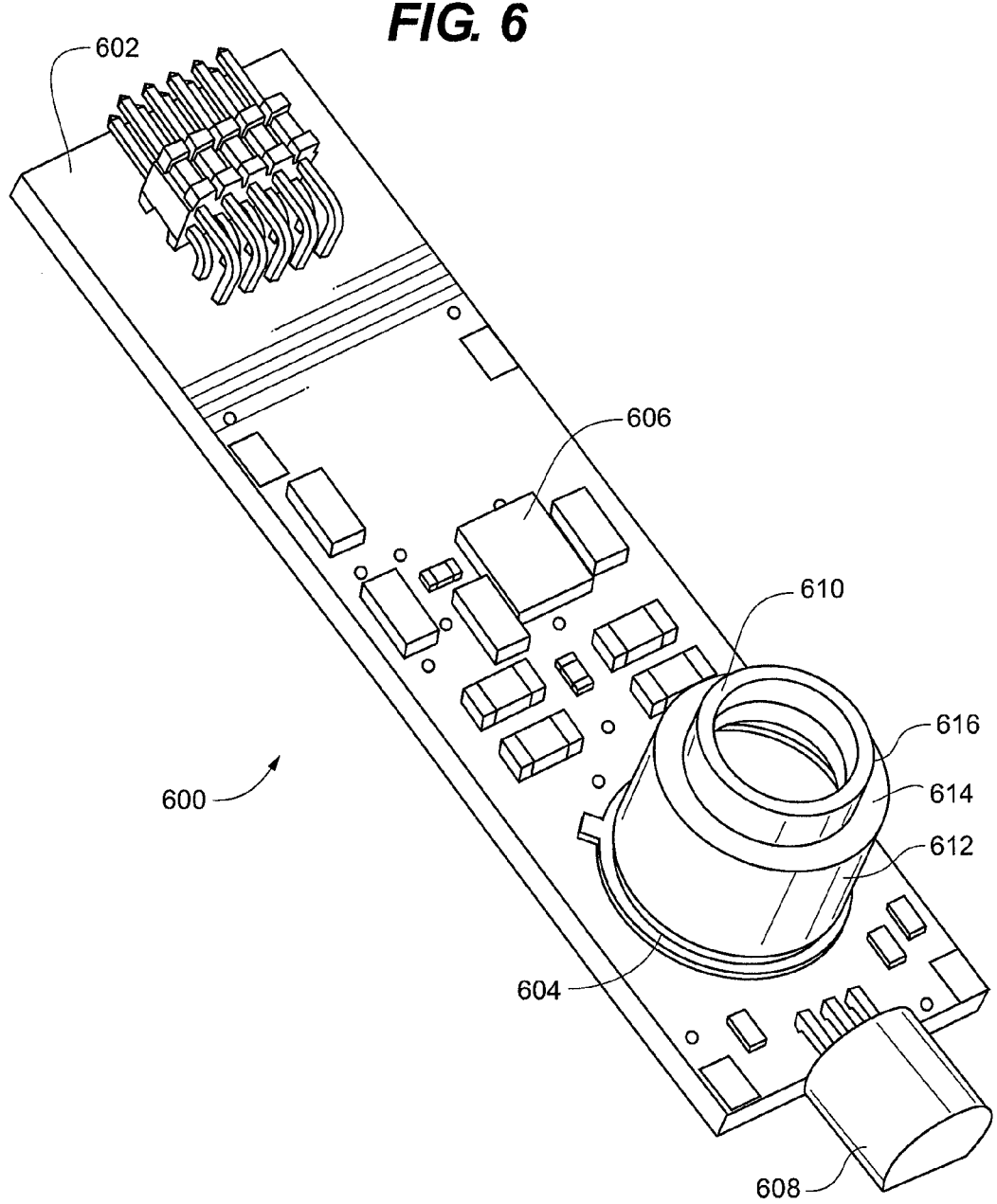
FIG. 6 is a perspective view of an emission detector board according to some embodiments of the invention.

FIG. 6 is a perspective view of an emission detector board 600 according to some embodiments of the invention. The detector board 600 generally includes a number of components, including an emission detector 604 positioned on a printed circuit board 602. In some embodiments of the invention, the emission detector 604 comprises a UV-sensitive photodiode. For example, the detector 604 may generate an intensity signal based on light from about 310 nm to about 400 nm that it detects from an analytical area outside the sensor head. The detector board 600 also includes a preamplifier 606 and a temperature sensor 608. An emission filter holder 610 positioned about the emission detector 604 supports one or more filters for screening the radiant energy and passing on the desired wavelengths to the detector 604. In the embodiment shown in FIG. 6, the filters include an interference filter 612 and a UG-11 glass filter 614. In some embodiments, an additional polyester film filter 616 is also positioned in front of the emission detector 604. In some cases the polyester film filter 616 has a thickness of about 0.5+/−0.2 mm. In some cases optical designs can provide increased optical efficiency (e.g., using ball lenses, highly divergent beams, etc.) but may also compromise the performance of interference filters which have a high efficiency and a high rejection value for collimated beams. Incorporating such a polyester film can in some cases minimize stray light levels to allow measurements of NDSA fluorescence in samples with a turbidity as high as 100. Nephelometric Turbidity Units (NTU).

Figure 7A:
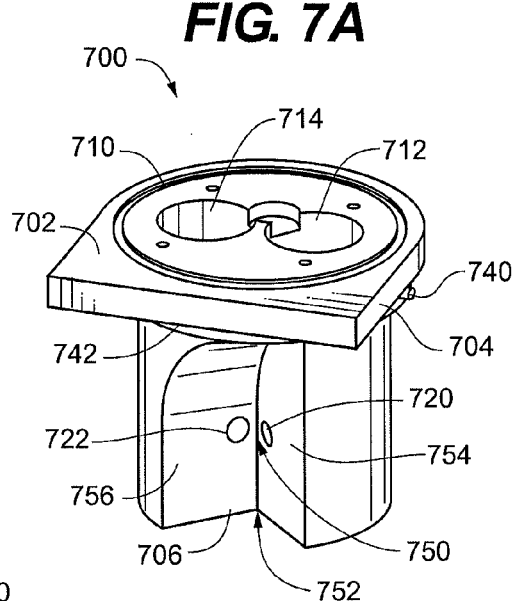
FIG. 7A is a top perspective view of a sensor head according to some embodiments of the invention.
Figure 7B:
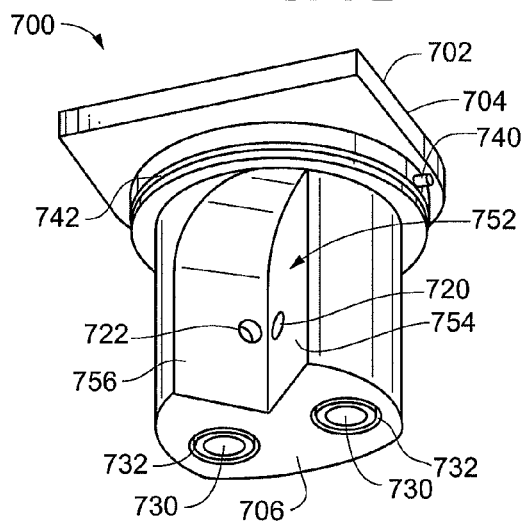
FIG. 7B is a bottom perspective view of the sensor head of FIG. 7A.
Figure 7C:
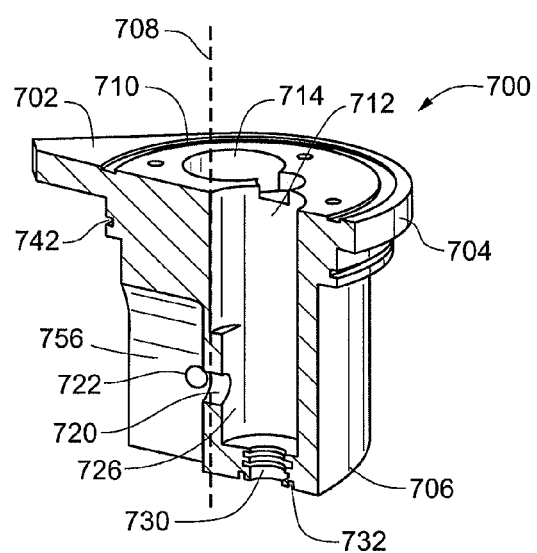
FIG. 7C is a perspective, cross-sectional view of the sensor head of FIG. 7A.

FIGS. 7A-7C present various views of a discrete immersible sensor head 700 according to some embodiments of the invention that can be attached to a controller module of a handheld fluorometer such as of those previously discussed. FIG. 7A is a top perspective view of the sensor head 700, FIG. 7B is a bottom perspective view of the sensor head 700, and FIG. 7C is a perspective, cross-sectional view of the sensor head 700. The sensor head 700 can be made from a plastic and may be molded and/or milled to achieve the desired shape and features.

In general, the sensor head 700 comprises a housing 702 that includes a first vertical cavity or chamber 712 that is configured to receive a light source circuit board (e.g., the light source board 320 of FIG. 3 or 500 of FIG. 5). In some cases the light source chamber 712 is formed with a cylindrical configuration, which can provide a snug fit for the cylindrical brass shields 326 illustrated in FIG. 3. In some embodiments the light source chamber 712 has a partially-cylindrical configuration including a planar wall 726 along one lateral side of the chamber 712. Returning to FIGS. 7A-7C, the sensor head housing 702 includes a second vertical cavity or chamber 714 for receiving an emission detector circuit board (e.g., the emission detector board 322 of FIG. 3 or 600 of FIG. 6), similar to the light source chamber 712. In some cases the light source chamber 712 and the emission detector chamber 714 may be formed and positioned symmetrically about a longitudinal axis 708 of the sensor head 700, although this is not required in all embodiments.

The sensor head housing 702 further includes an angular cutout 752 in the exterior surface of the housing 702. In some embodiments the angle of the cutout 752 is approximately 90 degrees, although it should be understood that the invention is not limited to a particular angle for the cutout. The cutout 752 is bounded by a first wall 754 intersecting a second wall 756 at the longitudinal axis of the sensor head 700. The first wall 754 defines a light source window 720 that provides a path through the first wall 754 for excitation energy emitted by the light source. The second wall 756 similarly defines a emission detector window 722 that provides a path through the second wall 756 for fluorescent emissions to reach the emission detector located within the sensor head housing 702. In some embodiments, the light source window 720 and/or the emission detector window 722 comprise a channel extending through the sensor head housing 702. In some embodiments the windows 720, 722 also include a lens, prism or other material optically transparent to the light source radiation and/or fluorescent emissions. For example, in some embodiments a glass or sapphire ball lens is positioned within each channel. Other suitable materials known in the art may also be used. The ball lens provides the light source/detector window, but also provides a focusing means for directing light between the light source/detector and an analytical area 750 outside the housing 702 of the sensor head 700.

As shown in the figures herein, the angular cutout 752, including the light source window 720 and the emission detector window 722, are oriented with respect to the controller module such that the angular cutout and the windows face toward the distal end of the controller module. As discussed further herein, the angular cutout and the windows may be oriented in a different direction in some embodiments. For example, in some embodiments the angular cutout and the windows face toward the proximal end of the controller module.

In some embodiments, the sensor head 700 includes a proximal end 704 and a distal end 706, between which extends the longitudinal axis 708 and a length of the sensor head 700. As shown in FIGS. 1 and 3, in some embodiments the sensor head 700 is connected to the bottom surface of the controller module housing at or near the proximal end 704 of the sensor head 700. In some cases the sensor head 700 may be fixedly attached to the controller housing with a fastener. The fastener can include, but is not limited to, screws, bolts, and/or pins, or an adhesive or weld (not shown in the figures). In some embodiments the sensor head 700 is secured with four screws that compress an O-ring positioned in a groove 710 between the sensor head 700 and the controller module. In some embodiments, the sensor head housing 702 may be integrally formed with the controller module such that there is a seamless transition between the proximal end 704 of the sensor head and the bottom surface of the controller module.

In some embodiments the sensor head 700 also includes part or all of a fastener that removably fastens a sample cup about the sensor head 700. As just one example, the fastener may comprise one or more pins 740 positioned about the sensor head housing 702 and corresponding slots on the sample cup. In some embodiments the pins 740 and the slots form a bayonet fastener that secures the sample cup about the sensor head and also aligns the sample cup in a preferred orientation (e.g., rotation) about the sensor head 700. Other fasteners (e.g., screw threads, opposing pressure elements, etc.) can also be included.

In some embodiments the sensor head 700 also includes holes 730 for inserting one or more temperature sensor covers, such as those depicted in FIG. 3. Returning to FIGS. 7A-7C, the holes 730 may be threaded or otherwise configured to receive and secure the temperature sensor covers. The temperature sensors (not shown in FIGS. 7A-7C) are adapted to sense the current temperature of the water sample and generate a corresponding signal that can be used to correct concentration calculations based on errors due to, e.g., temperatures outside an acceptable range.

In addition, the sensor head 700 is preferably an immersible sensor head, meaning that it is partly or wholly immersed below the surface of a water sample when taking fluorescent emission measurements. Accordingly, the sensor head housing 702, connection to the controller housing, and any windows or other potential voids in the housing 702 are effectively sealed prior to immersion. For example, in some cases the housing 702 includes a first O-ring groove 710 at the proximal end 704 of the sensor head and second O-ring grooves 732 around the temperature sensor holes 730. In some embodiments including a sample cup, a third O-ring groove 742 may also be formed around the circumference of the sensor head 700 near the proximal end 704 of the sensor head in order to provide a substantially impermeable seal between the sample cup and the sensor head 700. In addition, the light source window 720 and emission detector window 722 may also be sealed with O-rings and the like. In some embodiments, the light source window 720 and emission detector window 722 are sealed due to a pressure fit between the window channels and the ball lenses placed within the channels.

FIG. 8 is a flow diagram depicting a method of determining a concentration of a product in a water sample according to some embodiments of the invention. In general, the fluorometer measures a fluorescent light emission of the active molecule in the product that is proportional to the actual concentration of the product in the water sample. After providing a handheld fluorometer having a controller module and a sensor head connected to the controller module (802), a water sample containing the product of interest is provided. The sensor head is immersed in the water sample (804) and the water sample occupies an analytical area of the sensor. Next, an ultraviolet (UV) excitation light having a first UV wavelength is generated by a light source in the sensor head and directed into the water sample and the analytical area (806). The sensor head then detects and measures the fluorescent emissions of the sample at a second UV wavelength (808). The sensor head includes a controller (402 in FIG. 4, for example) that calculates the concentration of the product in the sample based on the measured fluorescent emissions (810). The first wavelength may be in the range of 280-310 nm. The second UV wavelength may be in the range of 310 nm to 400 nm. The sensor may also measure a reference fluorescence emission of the sample at the first wavelength. The sensor may also measure a fluorescence emission of a zero solution having zero concentration of the chemical. In that case, the concentration of the chemical in the sample may be calculated based on the calculated difference in the measured fluorescence emission of the sample containing the chemical and the measured fluorescence emission of the zero solution. The concentration of the sample may also be calculated based on a calibration constant determined for known concentrations of the product in a calibration sample.

As an example, in some cases sample concentrations may be evaluated based upon signals from two UV detectors. A reference detector measures an intensity of the UV excitation generated by the light source, while a fluorescent emission detector measures an intensity of the fluorescent emissions emitted by the product. The calculation uses the following equations:

$$C_C = K_X \left( \frac{I_E^S}{I_R^S} - \frac{I_E^0}{I_R^0} \right)$$

where $C_C$ is an actual, current concentration of a product X (for example, a surfactant, an antimicrobial agent, etc) in a sample solution;
$K_X$ is a calibration coefficient;
$I_E^S$ is an output signal from the emission detector for the sample solution;
$I_R^S$ is an output signal from the reference detector for the sample solution;
$I_E^0$ is an output signal from the emission detector for a zero solution (i.e., a solution with zero concentration of the product); and
$I_R^0$ is an output signal from the reference detector for the zero solution.

$$K_X = C_{CALIBR} \bigg/ \left( \frac{I_E^{CALIBR}}{I_R^{CALIBR}} - \frac{I_E^0}{I_R^0} \right)$$

where $C_{CALIBR}$ is a concentration of the product in a calibration solution;
$I_E^{CALIBR}$ is an output signal from the emission detector for the calibration solution; and
$I_R^{CALIBR}$ is an output signal from the reference detector for the calibration solution.

As discussed above with reference to FIG. 4, the controller 402 within the handheld fluorometer can calculate the concentration of the product in a sample based on the intensity signal from the emission detector. In some embodiments the controller 402 may also calculate the product concentration based on a calibration constant, zero shift, and/or an excitation reference signal using the relationships described above. Operation instructions for the controller may be stored in an onboard or discrete memory. In that respect, the memory may be a computer-readable medium comprising program instructions that cause the controller to provide any of the functionality ascribed to them, and perform any of the methods described herein. The controller may also store the raw fluorescence data obtained by the emission and/or reference detector(s) and other pertinent data in the memory. The controller may also store any calculated fluorescence values and/or concentration data in the memory.

As discussed above, in some embodiments of the invention fluorescence measurements can be taken by a handheld fluorometer by manually lowering the sensor head into a water sample. For example, a user can grasp the controller module and temporarily dip the immersible sensor head into a liquid sample such that the sensor head is partially or completely immersed in the sample and the water sample occupies the analytical area near the sensor head windows. A similar method can be used to measure other optical properties of a water sample using one or more optical measuring devices (in addition to fluorometric devices) configured in a similar manner to embodiments of the invention previously discussed herein. For example, a turbidimeter and/or an absorbance meter may include a handheld controller module similar to those discussed above along with an immersible sensor head incorporating turbidity and/or absorbance measuring sensors and optics.

Turning now to FIGS. 9-10, in some embodiments a sampling member including a sample cup is provided to contain a water sample about the immersible sensor head. A small volume of water from about 5 ml to about 20 ml can be sufficient for taking measurements in some embodiments. Such handheld devices are thus extremely portable, being able to measure one or more properties of a water flow while being removed from the source of the water sample. For example, in some embodiments the handheld optical device is a handheld fluorometer that can be used to measure fluorescent emissions in the field or in a laboratory environment.

Embodiments of the invention are thus useful in many applications similar to those targeted by traditional cell-based instruments (e.g., in which a water sample is placed within an optically transparent cell). Embodiments of the invention, however, provide a number of advantages over cell-based devices. For example, the sensor head of the handheld device described herein can be immersed within the water sample, while cell-based devices typically rely on instrumentation located exterior to the cell to measure properties of the water within the cell. Accordingly, the handheld devices herein avoid drawbacks associated with an optical cell such as signal degradation due to scratching or fouling of the cell surface. Similarly, minimal cleaning (e.g., of the small area of the light source and emission detector windows in the fluorometers described above) can be contrasted with the time consuming cleaning or replacement usually required for optical cells. In addition, embodiments of the invention provide enhanced sensitivity due in part to the immediate proximity of the water sample to the immersible sensor head, which dramatically decreases the travel distance between optical sensor(s) located within the sensor head and the water sample. Accordingly, the heightened sensitivity provided in embodiments of the invention provides advantages over past handheld optical measuring devices. For example, a fluorometer according to embodiments of the invention can measure very low concentrations of product (e.g., parts per million, ppm) and/or for measuring concentrations of product within a water sample having high color and/or turbidity.

FIGS. 9A-9D are various views of a handheld optical measuring device 900 according to some embodiments of the invention. The optical measuring device 900 generally includes a controller module 902 incorporating an immersible sensor head 906 and a sampling member 904 having a sample cup 908 for containing a water sample to be measured. In some embodiments the sampling member 904 is advantageously coupled to the controller module 902, thus providing an integral and convenient manner of obtaining and containing a water sample, while also providing a protective shell or cover for the immersible sensor head 906 during use and/or when not in use. In some embodiments the attached nature of the sample cup can allow measurements of the scooped sample with minimal delay and without additional preparation or handling steps.

Figure 9B:
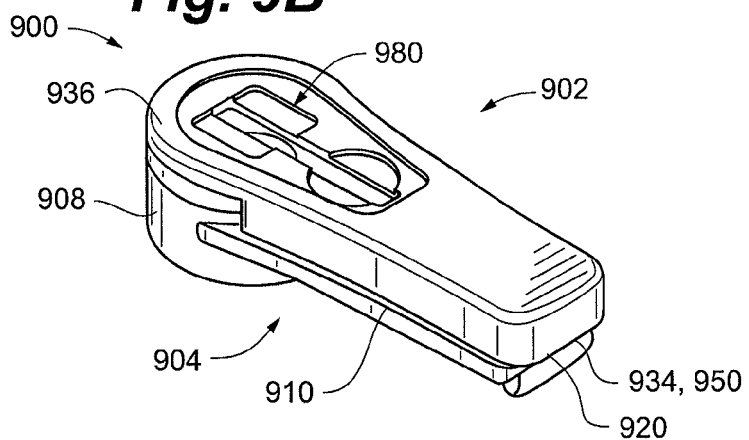
FIG. 9B is a perspective view of the optical measuring device of FIG. 9A in a closed position.

FIG. 9A is a perspective view of the handheld optical measuring device 900 with the sampling member 904 in an open position. The handheld controller module 902 generally includes a housing 930 having a bottom surface 932 that is connected to the sensor head 906. The housing is preferably adapted to be held by a user's hand. For example, the housing may be an elongated housing having the form of a wand or handle. Referring to FIG. 9B, in some embodiments the housing 930 has a face 980 that may include a display and/or an input interface such as a keypad, buttons, etc. (not shown in FIG. 9B). Although not shown, the controller module 902 includes a controller positioned within the housing 930 that is adapted to calculate an optical property of a water sample based on an optical sensor signal received from at least one optical sensor located within the sensor head. As just one example, the optical sensor can include a fluorescent emission detector and the controller may receive an optical signal indicative of a level of fluorescence in the water sample and calculate a corresponding concentration of a product in the water sample as described in embodiments of a fluorometer described herein above. In some embodiments the optical sensor may also, or in the alternative, include a turbidity sensor and/or absorbance sensor.

Returning to FIG. 9A, in some embodiments the immersible sensor head 906 includes a proximal end 942 and a distal end 940 between which extends a length of the sensor head 906. The proximal end 942 of the sensor head 906 is connected to the bottom surface 932 of the controller housing with the distal end 940 of the sensor head extending out away from the surface 932 of the housing 930. As just one example, in some cases the controller module housing 930 has a distal end 936 and a proximal end 934 between which extends a length of the controller module housing 930, with the sensor head 906 positioned proximate to the distal end 936. The proximal end 934 of the controller module housing can be adapted to be held by the user's hand.

In some embodiments the sampling member 904 includes both the sample cup 908 and an attachment member 910 that couples the sample cup 908 to the controller module 902. In some embodiments the attachment member 910 is an elongated member that couples and/or retains the sample cup to/with the controller module. For example, the attachment member 910 may be an elongated rigid member with a first end 952 coupled to the sample cup 908 and a second end 950 coupled to the controller module 902. A length of the attachment member 910 extends between the first and the second ends 952, 950.

In some cases the attachment member 910 is integral with the sample cup 908 and movably coupled to the controller module 902, although different embodiments may include an attachment member integral with the controller module 902 and/or attached to the sample cup 908. The attachment member 910 can be coupled to the controller module 902 in a variety of manners. As just one example, in some cases the second end 950 of the attachment member 910 is hingedly coupled about a pivot 920 to the proximal end 934 of the controller module portion. In some cases the attachment member may pivot about an axis of rotation 922 substantially parallel to the bottom surface 932 of the housing controller, although other configurations are also possible.

Figure 9C:
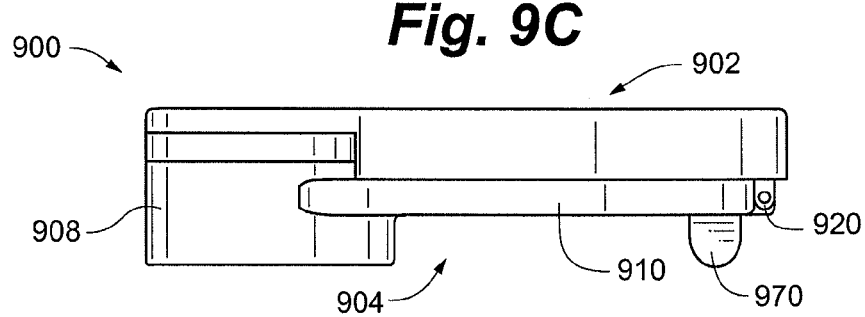
FIG. 9C is a side view of the optical measuring device of FIG. 9A in a closed position.
Figure 9D:
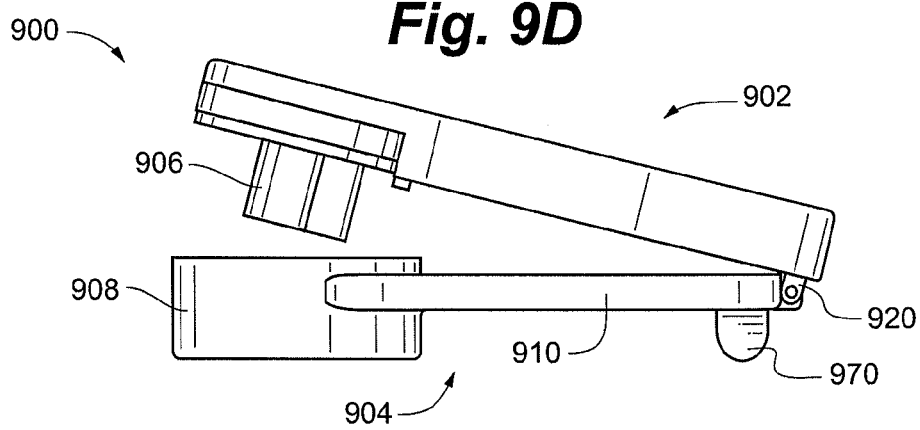
FIG. 9D is a side view of the optical measuring device of FIG. 9A in a partially open position.

The sample cup 908 is configured to contain a water sample to be analyzed by the immersible sensor head 906 on the controller module 902. Turning to FIGS. 9B-9D, in some embodiments the sample cup 908 can completely surround the sensor head 906 in a closed position of the handheld device 900. In some cases the sample cup 908 is removably fastenable about the sensor head 906. For example, as shown in FIG. 9A, in some embodiments the sample cup 908 and the controller module/sensor head include cooperating fasteners (e.g., post 960A and hole 960B and/or nubs 962A and sample cup rim 962B) that removably fasten the sample cup 908 about the sensor head 906. Those skilled in the art will appreciate a variety of fasteners are available and the invention is not limited to any particular fastener. In some embodiments air escapes the sample cup as the sample cup is fastened about the sensor head and the sensor head 904 displaces air and water within the sample cup. This helps reduce or eliminate pockets of air that can be trapped within the sample cup and affect fluorescence measurements. Further, in some cases an O-ring (not shown) or other sealing mechanism can help contain the water sample within the sample cup 908 when it is fastened about the sensor head 906. In some embodiments the sample cup 908 may not be sealed to allow further air to escape from the sample cup. Returning to FIGS. 9B-9D, assuming a water sample is present in the sample cup 908, the sensor head will extend at least partially into the water sample as the sample cup closes over the sensor head 906, thus assuring that at least the portion of the sensor head receiving and/or transmitting light from/into the sample is immersed in the water sample.

Accordingly, the sample cup 908 can also provide a protective enclosure for the sensor head 906 when it is fastened about the sensor head 906. In some embodiments the sample cup 908 is made from a rigid plastic, which provides a durable and sturdy protective shell or cover for the sensor head 906. Other materials known in the art and having similar properties are also contemplated.

As mentioned above, the immersible sensor head 906 can include one or more of a variety of optical sensors, including optical sensors useful for measuring fluorescence, turbidity, and/or absorbance within a liquid sample. In many cases the sensor head may also include a light source that emits light of a particular wavelength into to facilitate measurements of different optical properties. In turn, the optical sensor(s) may be sensitive to one or more specific ranges of light wavelengths, depending upon the configuration of the sensor. In some embodiments the sample cup 908 comprises a material that is opaque to the light wavelengths to which the optical sensor is sensitive. In some embodiments, the sample cup material is opaque to light wavelengths generated by a light source within the sensor head. As just one example, in some embodiments the sample cup 908 may be opaque to UV radiation within a range from about 280 nm to about 320 nm and within a range from about 300 nm to about 420 nm useful for embodiments of the fluorometer described above. In some embodiments a clear polycarbonate can be used to provide protection from ambient light and allow visual control of the water sample level.

Referring to FIGS. 9C and 9D, in some embodiments the sample cup 908 and the attachment member 910 combine to form a substantially stable base for the optical device 900 upon a support surface (not shown). For example, a bottom portion of the sample cup 908 can provide a first footing upon the support surface and the attachment member 910 may include a support member 970 at its second end 952 providing a second footing. In some cases the geometry of the sample cup 908 and/or the support member 970 may be configured to provide a substantially flat footing such that the attachment member 910 and/or the controller module housing 930 are substantially parallel with respect to the support surface. In some embodiments, however, the sample cup and/or support member may be configured such that the controller module is angled with respect to the support surface. Such a configuration can aid in viewing a display on the controller module face 980.

Figure 9E:
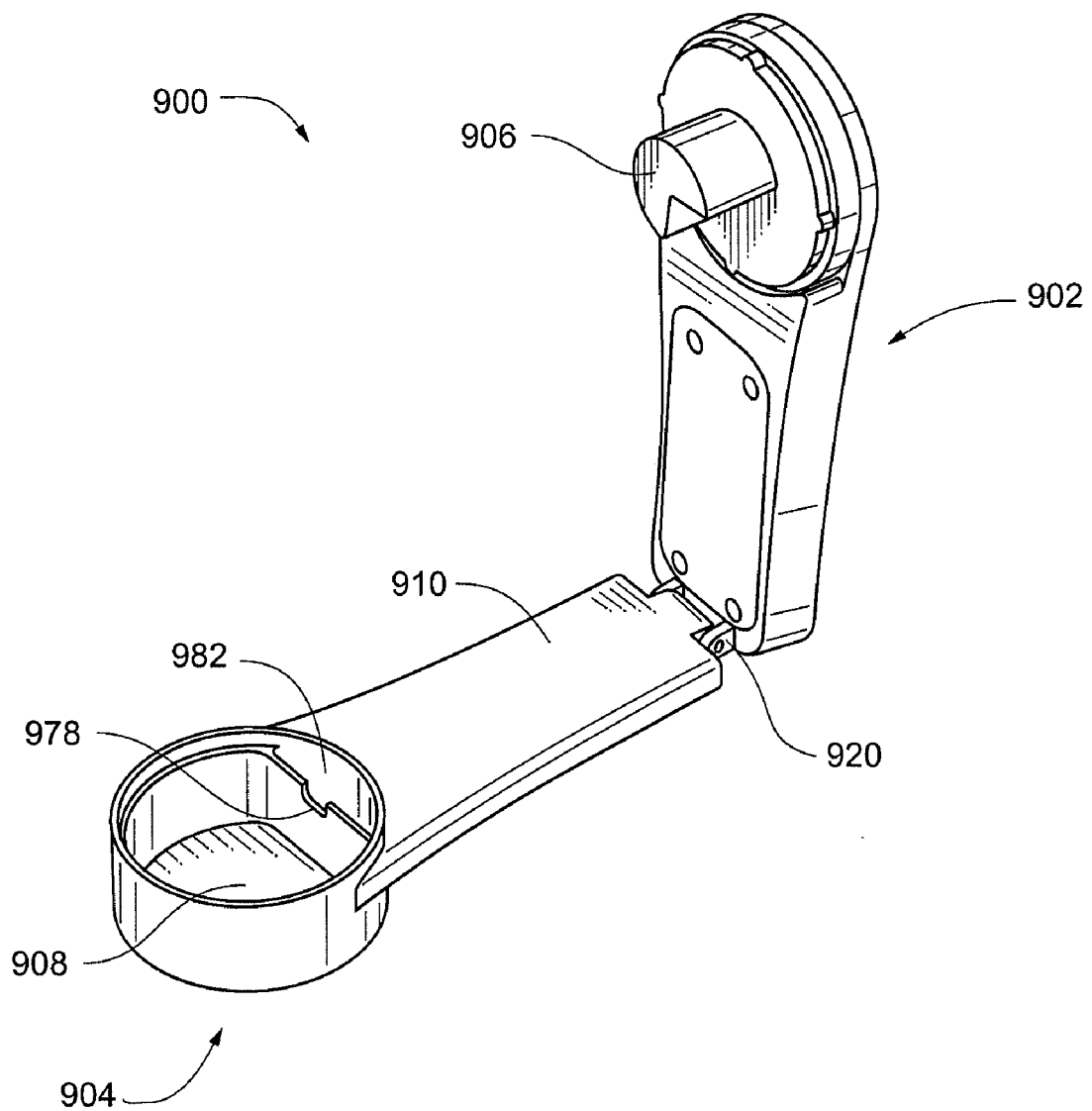
FIG. 9E is a perspective view of an optical measuring device with an overfill reservoir according to some embodiments of the invention.

In some embodiments, an overfill outlet or opening provides a path out of the sample cup 908 for excess sample water when the sensor head is inserted into the sample cup 908. In some embodiments the overfill outlet is advantageously located out of line of sight of a portion of the sensor head 906 having sensor optics to minimize any potential effect on measurements from stray light entering the sample cup 908 through the overfill opening. In some embodiments the optical measuring device 900 further includes an overfull reservoir or cavity, coupled to the overfill opening, that can receive a portion of the water sample from the sample cup 908. For example, the overfill reservoir may be a separate chamber coupled to the sample cup 908 or a portion of a slightly larger sample cup. In some embodiments the attachment member 910 may include the overfill reservoir with the overfill opening adjacent the first end 952 of the attachment member 910. FIG. 9E shows an example of an optical measuring device 900 with an overfill outlet 978 connecting the sample cup 908 with an overfill reservoir 982 according to some embodiments of the invention.

FIG. 10 illustrates a flow diagram showing a method 1000 for measuring an optical property of a water sample according to some embodiments of the invention. In a first step 1002, a handheld optical device is provided to conduct the measurements. The device preferably includes a controller portion with a sensor head and a sampling portion having a sample cup. In some embodiments the device comprises one of the handheld optical devices described herein, although any device having features of the invention may be used. For example, the optical device may be adapted to measure one or more different optical properties of a water sample, such as a fluorescence, turbidity, or absorbance of the water sample. Other optical properties are also contemplated.

In a second step 1004, the method includes unfastening a sample cup from about the sensor head of the handheld optical device. The sample cup is then filled 1006 with a water sample of sufficient volume, and fastened 1008 back about the sensor head. Some embodiments allow a user to easily use the cup for acquiring a water sample. For example, a user can unfasten the sample cup 908, move it away from the sensor head 906, and then pour a water sample into the cup. In some embodiments, the user can use the cup 908 to scoop a water sample from a larger reservoir or container. For example, the user can first open the device by pulling the attachment member 910 away from the controller module 902. The user can then hold onto the attachment member and/or controller portion to scoop water. In some embodiments the attachment member may be rotated into a 180 degree orientation with respect to the controller portion 902, and a user can grasp the controller portion 902 in order to extend the length of the device when acquiring a sample. The attachment member can thus provide an extended handle, making it easier to grab or scoop a water sample from an open body of water.

With the sample cup fully fastened about the sensor head, the sensor head is at least partially immersed in the water sample. In some embodiments, the sample cup preferably remains coupled to the controller portion of the device throughout the unfastening and fastening about the sensor head. Upon fastening the sample cup about the sensor head, the method also includes measuring 1010 an optical property of the water sample with the sensor head and the controller portion.

In some embodiments, the method further includes rotating the sampling portion away from the controller portion and the sensor head prior to introducing the water sample into the sample cup. For example, referring to FIG. 9D, the sampling portion 904 can be rotated away from the controller module 902 until the device is open and the sample cup 908 is accessible. FIG. 9A shows one example of an open configuration. After measuring the optical property or properties from the water sample, the sample cup can be unfastened and opened to discard the water sample from the sample cup. The sample cup can then again be fastened about the sensor head to provide a protective cover about the sensor head.

Thus, embodiments of the invention are disclosed. Although the present invention has been described in considerable detail with reference to certain disclosed embodiments, the disclosed embodiments are presented for purposes of illustration and not limitation and other embodiments of the invention are possible. One skilled in the art will appreciate that various changes, adaptations, and modifications may be made without departing from the spirit of the invention and the scope of the appended claims.

What is claimed is:

1. A handheld optical measuring device, comprising:
    a handheld controller module comprising
        a housing comprising a bottom surface, the housing adapted to be held by a user's hand,
        a controller positioned within the housing, the controller adapted to calculate an optical property of a water sample based on an optical sensor signal, and
        an immersible sensor head comprising
            a housing comprising a proximal end and a distal end between which extends a length of the sensor head, the sensor head being connected to the bottom surface of the controller module housing at the proximal end of the sensor head housing, and
            at least one optical sensor coupled to the controller, the optical sensor adapted to generate and transmit the optical sensor signal to the controller based on the optical property of the water sample when the sensor head is immersed in the water sample; and
    a sampling member comprising
        a sample cup for containing the water sample, the sample cup being removably fastenable about the sensor head such that the water sample can be introduced into the sample cup when the sample cup is not fastened about the sensor head and such that at least a portion of the sensor head is immersed in the water sample when the sample cup containing the water sample is fastened about the sensor head, and
        an attachment member coupled to the sample cup and the handheld controller module for retaining the sample cup with the handheld controller module whether or not the sample cup is fastened about the sensor head.

2. The device of claim 1, wherein the controller module housing further comprises a first end and a second end between which extends a length of the controller module housing, wherein the sensor head is positioned proximate to the first end of the controller module housing and wherein the second end of the controller module housing is adapted to be held by the user's hand.

3. The device of claim 2, wherein the attachment member comprises a support member, wherein the sample cup and the support member provide a substantially stable base for the handheld optical measuring device in a stationary position upon a support surface.

4. The device of claim 1, wherein the attachment member comprises a rigid member hingedly coupled to the controller module housing.

5. The device of claim 4, wherein the attachment member is integral to the sample cup.

6. The device of claim 1, wherein the sampling member further comprises an overfill reservoir that can receive a portion of the water sample from the sample cup.

7. The device of claim 6, wherein the attachment member comprises the overfill reservoir.

8. The device of claim 1, wherein the sampling member provides a rigid, protective cover around the sensor head when the sample cup is fastened about the sensor head.

9. The device of claim 1, wherein the optical measuring device is at least one of a fluorometer, a turbidimeter, and an optical absorbance meter.

10. The device of claim 1, wherein the optical sensor is sensitive to a first wavelength range of light, and wherein the sample cup is opaque to the first wavelength range of light.

11. A handheld optical measuring device, comprising:
    a controller portion;
    a sampling portion; and
    a pivot coupling the controller portion and the sampling portion,
    the controller portion comprising
        an elongated rigid housing comprising a bottom surface, and a first end and a second end between which extends a length of the controller portion housing,
        a controller adapted to calculate an optical property of a water sample based on an optical sensor signal, and
        an immersible sensor head comprising at least one optical sensor coupled to the controller and a proximal end and a distal end between which extends a length of the sensor head, the proximal end of the sensor head being connected to the bottom surface of the controller portion housing proximate to the first end of the controller portion housing; and
    the sampling portion comprising
        an elongated rigid attachment member comprising a first end and second end between which extends a length of the attachment member, the pivot coupling the second end of the attachment member to the second end of the controller portion housing, and
        a sample cup for receiving the water sample, the sample cup coupled to the first end of the attachment member, the sample cup further being removably fastenable about the sensor head such that the sensor head is at least partially immersed in the water sample contained in the sample cup with the sample cup fastened about the sensor head.

12. The device of claim 11, wherein the pivot comprises an axis of rotation substantially parallel to the bottom surface of the controller housing.

13. The device of claim 11, wherein the attachment member comprises a support member, wherein the sample cup and the support member provide a substantially stable base for the handheld optical measuring device in a stationary position upon a support surface.

14. The device of claim 11, wherein the sampling portion further comprises an overfill reservoir that can receive a portion of the water sample from the sample cup.

15. The device of claim 14, wherein the attachment member comprises the overfill reservoir.

16. The device of claim 11, wherein the sampling portion provides a rigid, protective cover around the sensor head when the sample cup is fastened about the sensor head.

17. The device of claim 11, wherein the optical measuring device is at least one of a fluorometer, a turbidimeter, and an optical absorbance meter.

18. A method for measuring an optical property of a water sample, comprising:
providing a handheld optical measuring device having a controller portion comprising an immersible sensor head, and a sampling portion comprising a sample cup and an attachment member coupling the sample cup to the controller portion, the sample cup being removably fastenable about the sensor head;
unfastening the sample cup from about the sensor head, the sample cup remaining coupled to the attachment member and the controller portion;
introducing a water sample into the sample cup;
fastening the sample cup about the sensor head such that at least part of the sensor head is immersed in the water sample; and
measuring an optical property of the water sample with the sensor head and the controller portion.

19. The method of claim 18, further comprising rotating the sampling portion away from the controller portion and the sensor head prior to introducing the water sample into the sample cup.

20. The method of claim 18, further comprising removing the water sample from the sample cup and fastening the sample cup about the sensor head to provide a protective cover about the sensor head.

21. The method of claim 18, wherein the optical property is a fluorescence, turbidity, or absorbance of the water sample.

22. The method of claim 18, wherein the handheld optical measuring device is the handheld optical measuring device according to claim 11.

* * * * *